(12) United States Patent
Liu et al.

(10) Patent No.: US 7,169,183 B2
(45) Date of Patent: Jan. 30, 2007

(54) VERTEBRAL IMPLANT FOR PROMOTING ARTHRODESIS OF THE SPINE

(75) Inventors: Mingyan Liu, Bourge la Riene (FR); Hans-Joachim Früh, Deggendorf (DE); Harald Ebner, Deggendorf (DE); Bradley T. Estes, Durham, NC (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 71 days.

(21) Appl. No.: 10/242,642

(22) Filed: Sep. 12, 2002

(65) Prior Publication Data

US 2003/0023306 A1    Jan. 30, 2003

(51) Int. Cl.
*A61F 2/44* (2006.01)
(52) U.S. Cl. ..................................... 623/17.16
(58) Field of Classification Search ... 623/17.11–17.16
See application file for complete search history.

(56) References Cited

U.S. PATENT DOCUMENTS

| | | |
|---|---|---|
| 4,349,921 A | 9/1982 | Kuntz |
| 4,834,757 A | 5/1989 | Brantigan |
| 4,936,848 A | 6/1990 | Bagby |
| 5,015,247 A | 5/1991 | Michelson |
| 5,062,845 A | 11/1991 | Kuslich et al. |
| 5,190,548 A | 3/1993 | Davis |
| 5,250,061 A | 10/1993 | Michelson |
| 5,304,191 A | 4/1994 | Gosselin |
| 5,306,309 A | 4/1994 | Wagner et al. |
| 5,425,772 A | 6/1995 | Brantigan |
| 5,443,514 A | 8/1995 | Steffee |
| 5,445,639 A | 8/1995 | Kuslich et al. |
| 5,458,638 A | 10/1995 | Kuslich et al. |
| 5,484,437 A | 1/1996 | Michelson |
| 5,499,984 A | 3/1996 | Steiner et al. |
| 5,609,635 A | 3/1997 | Michelson |
| 5,609,636 A | 3/1997 | Kohrs et al. |
| 5,607,424 A | 4/1997 | Tropiano |

(Continued)

FOREIGN PATENT DOCUMENTS

DE    3630863    3/1988

(Continued)

*Primary Examiner*—Bruce Snow
*Assistant Examiner*—Cheryl Miller
(74) *Attorney, Agent, or Firm*—Krieg DeVault, LLP

(57) ABSTRACT

This invention provides a vertebral implant for impaction in a disc space to restore and/or maintain desired disc space height and spinal orientation. The implant has an elongated basis body having a generally lens-shape provided by convex upper and lower surfaces. Bearing surfaces are provided on the cross-edge surfaces of the endwalls. Grooves are provided in the upper and lower surfaces positioned between the bearing surfaces. The implant can be prepared from a wide variety of materials including metallic materials, synthetic materials, polymeric materials, ceramic materials, and composite materials including reinforced materials i.e. glass, fiber, and/or carbon fiber reinforced materials (CFRP). These preferred materials for fabricating implants in the present invention reduce costs, increase service life and provide excellent physiological compatibility. The non-metallic material can be selected to be either a substantially permanent material, a biodegradable material or a bioerodable material. Further, the implant material can be provided to be radio opaque to facilitate monitoring of bone ingrowth both into the implant and between the opposing endplates of the adjacent vertebrae.

42 Claims, 9 Drawing Sheets

U.S. PATENT DOCUMENTS

| | | |
|---|---|---|
| 5,649,945 A | 7/1997 | Ray et al. |
| 5,669,909 A | 9/1997 | Zdeblick et al. |
| 5,683,463 A | 11/1997 | Godefroy et al. |
| 5,697,977 A | 12/1997 | Pisharodi |
| 5,720,749 A | 2/1998 | Rupp |
| 5,766,252 A | 6/1998 | Henry et al. |
| 5,776,199 A | 7/1998 | Michelson |
| 5,782,830 A | 7/1998 | Farris |
| 5,846,244 A | 12/1998 | Cripe |
| 5,857,995 A | 1/1999 | Thomas et al. |
| 5,888,224 A | 3/1999 | Beckers et al. |
| 5,888,227 A | 3/1999 | Cottle |
| 5,893,890 A | 4/1999 | Pisharodi |
| 6,059,829 A | 5/2000 | Schlapfer et al. |
| 6,080,158 A | 6/2000 | Lin |
| 6,083,225 A | 7/2000 | Winslow et al. |
| 6,159,214 A | 12/2000 | Michelson |
| 6,245,108 B1* | 6/2001 | Biscup .................... 623/17.11 |
| 6,258,125 B1* | 7/2001 | Paul et al. ............... 623/17.11 |
| 6,277,149 B1* | 8/2001 | Boyle et al. ............. 623/17.16 |
| 6,290,724 B1* | 9/2001 | Marino .................... 623/17.11 |
| 6,325,827 B1* | 12/2001 | Lin .......................... 623/17.16 |
| 6,395,035 B2* | 5/2002 | Bresina et al. ........... 623/17.15 |
| 6,423,095 B1 | 7/2002 | Van Hoeck et al. |
| 6,610,089 B1 | 8/2003 | Liu et al. |
| 6,746,484 B1 | 6/2004 | Liu et al. |

FOREIGN PATENT DOCUMENTS

| | | |
|---|---|---|
| EP | 0195455 | 3/1986 |
| EP | 0276153 | 7/1988 |
| EP | 0493698 | 7/1992 |
| EP | 0637440 | 2/1995 |
| EP | 0646366 | 4/1995 |
| EP | 0796593 | 9/1997 |
| EP | 0834295 | 4/1998 |
| FR | 2724312 | 3/1996 |
| FR | 2727004 | 5/1996 |
| FR | 2736538 | 1/1997 |
| FR | 2760355 | 3/1997 |
| FR | 2742044 | 6/1997 |
| FR | 2742653 | 6/1997 |
| FR | 2767675 | 3/1999 |
| WO | WO 94/10927 | 5/1994 |
| WO | WO 95/08306 | 3/1995 |
| WO | WO 96/27348 | 9/1996 |
| WO | WO 97/06753 | 2/1997 |
| WO | WO 97/14378 | 4/1997 |
| WO | WO 97/23174 | 7/1997 |
| WO | WO 98/04202 | 2/1998 |
| WO | WO 98/09586 | 3/1998 |
| WO | WO 99/09913 | 3/1999 |
| WO | WO 01/28465 A2 | 4/2001 |

* cited by examiner under 35 U.S.C. 154(b) by 362 days.

VERTEBRAL IMPLANT FOR PROMOTING ARTHRODESIS OF THE SPINE

CROSS-REFERENCE TO RELATED APPLICATIONS

The present application claims the benefit of German Utility Model Application 200 04 693.4, filed on Mar. 14, 2000, and PCT Application No. U.S./01/08073 filed on Mar. 14, 2001, which are hereby incorporated by reference in their entirety.

TECHNICAL FIELD

This invention relates to an intervertebral implant for treatment of spinal deformities. More preferably, this invention is directed to a metallic or synthetic, intervertebral implant for implantation into a prepared disc space to facilitate spinal fusion, maintain desired disc space height, and/or spinal orientation.

BACKGROUND

For degenerated, diseased or otherwise damaged spinal columns and vertebrae, it is known to treat these defects by removal of all or a portion of the vertebral disc and inserting an implant such as a spinal implant to restore normal disc height and spine orientation, and repair the spinal defects. When desired, osteogenic material also can be implanted into the intervertebral space to enhance arthrodesis, or spinal fusion between the two vertebrae adjacent to the intervertebral space. Selected implants are formed to provide a cavity for receipt of the osteogenic material.

The spinal column can exert considerable force on the individual vertebrae, and consequently also on any implant implanted in between the vertebrae. Often for defective or diseased vertebrae the bone tissue in the center of the endplate, where the vertebral body is normally only covered by a thin cortical bone layer, is weakened. The strength and integrity of the endplate may be compromised. Implants inserted in between these weakened bone tissue can subside or sink into the vertebral body. This results in a failure to maintain the desired disc space height and causes tremendous pain to the patient.

Additionally, arthrodesis or fusion of the vertebrae adjacent is recommended to treat a damaged disc or diseased vertebra. Spinal implants typically are formed of a metal such as titanium or surgical steel. While the selection of the implant configuration and composition can depend upon a variety of considerations, for arthrodesis it is often desirable to select a material that does not stress shield the bone ingrowth. Titanium and surgical steel provide the requisite strength to maintain correct disc space height and orientation; however, some evidence exists that these materials may stress shield the bone. Bone and bone derived material can provide an acceptable material having the similar strength and compressibility as living bone tissue. However, suitable donor bone is scarce. Further, extensive screening and testing must be strictly performed to minimize any risk either real or perceived for the transmission of infections from the donor to the recipient.

The following are representative of the current state of the art for the relevant technology.

A vertebral implant is described in WO-95/08306 issued to Beckers (U.S. Pat. No. 5,888,224). Intervertebral implant comprises an elongated body formed of a titanium or titanium alloy material and having a shape that is basically lens-shaped with a width less than its height and provided with or without an internal cavity. Implantation of the implant requires distraction of the adjacent vertebral bodies, insertion of the implant, which is then rotated about its longitudinal axis.

Another vertebral implant is described in U.S. Pat. No. 4,834,757 issued to Brantigan. This vertebral implant has a parallelepiped shape and comprises an outer surface completely covered with nubs or barbs that are embedded into the channel cut into the endplates.

An intervertebral implant is described in WO 96/27348 (U.S. Pat. No. 6,059,829) issued to Schlapfer et al.; the implant consists essentially of a frame about an internal cavity and includes longitudinal sidewalls having perforations therethrough. The frame is open without restriction on the top and bottom. The upper and lower surfaces are convex and join the longitudinal sidewalls and the two endwalls of the frame at sharp edges.

Another implant that is described in FR 7/10664 issued to Liu et al. This metallic implant has upper and lower surfaces that include paired projections extending vertically from these surfaces for cutting into and piercing the cortical endplate in opposing intervertebral bodies without resting on soft cancellous bone. The upper and lower surfaces also include pairs of opposed bearing surfaces to contact the uncompromised cortical bone portion of vertebral bodies.

In light of the aforementioned described problems for treating spinal defects, there is a continuing need for advancements in the relative field, including treatment of damaged or diseased spinal columns, improved implants, selection of suitable materials from which implants can be formed and methods of promoting bone fusion between the adjacent vertebrae. The present invention is such an advancement and provides a wide variety of benefits and advantages.

DISCLOSURE OF THE INVENTION

The present invention relates to intervertebral implants, the manufacture and use thereof. Various aspects of the invention are novel, nonobvious, and provide various advantages. While the actual nature of the invention covered herein can only be determined with reference to the claims appended hereto, certain forms and features, which are characteristic of the preferred embodiment disclosed herein, are described briefly as follows.

This invention provides an intervertebral implant or spacer for implantation into a prepared disc space. The intervertebral implant can be made of a metallic or a synthetic, non-metallic material, such as, a polymeric material, a ceramic material, or a reinforced composite. In one form, this intervertebral implant comprises an elongate body having an internal cavity. The cavity can serve as a depot for osteogenic material or spongioseum bone material to facilitate the spinal fusion of the vertebral bodies adjacent to the disc space. The implant body is bordered by two longitudinal walls or sidewalls and by two frontal or endwalls located opposite one another. Upper and lower surfaces extend laterally between the longitudinal walls. The upper and lower surfaces include openings into the inner cavity. Crosswise-extending edge surfaces of the endwalls and longitudinal walls surface define contact surfaces or bearing surfaces.

In one preferred embodiment the opposite frontal walls or endwalls are formed to be thicker than the pair of opposite longitudinal walls, thereby widening the cross-edge extending surfaces. The cross-edge surfaces are preferably formed as integral parts of the opposing endwalls.

In another form the present invention provides an intervertebral implant provided for implantation into a disc space between adjacent vertebrae. The implant comprises an elongate body defining a longitudinal axis and at least one tissue-receiving groove extending transverse to the longitudinal axis. The implant comprises: also includes: a cavity bounded by a first endwall and an opposite second endwall, the first endwall defining a first bearing surface and an opposite second bearing surface and the second endwall defining a third bearing surface and an opposite fourth bearing surface; an upper surface extending between the first endwall and the second endwall, the upper surface having an arcuate portion adapted to bear against an inferior endplate of a first vertebra; and an opposite lower surface extending between the first endwall and the second endwall, the lower surface having an arcuate portion adapted to bear against a superior endplate of a second vertebrae. In preferred embodiments the first and second endwalls have a first thickness measured along the longitudinal axis that is thicker than either the thickness of the longitudinal walls or the thickness of the upper and lower surfaces.

In another form, the present invention provides an implant for promoting fusion between adjacent vertebra. The implant comprises: an elongate body defining a longitudinal axis and having an opening extending therethrough transverse to the longitudinal axis. The body comprises: a first supporting endwall terminating the body on a first end; an opposite second supporting endwall terminating the body on a second end, the first and second supporting endwalls positioned substantially transverse to the longitudinal axis and adapted to bear against cortical bone tissue in opposing endplates of the adjacent vertebrae, a first sidewall and an opposite second sidewall interconnecting the first supporting wall and the second supporting wall, wherein the body includes at least one tissue receiving groove extending from the first sidewall to the second sidewall.

The preferred embodiments the intervertebral implant includes endwalls that are thicker than the longitudinal walls. (The endwalls terminate in cross-edge or peripheral surfaces extending transverse to the longitudinal walls. The peripheral surfaces are wider than the cross-edge surfaces of the longitudinal walls.) The peripheral surfaces provide wide contact or supporting surfaces for bearing against the cortical portions of the adjacent vertebral bodies such as found in and about the cortical ring or the apophyseal ring structure. Cortical bone tissue is either harder and/or denser than the cancelleous bone or spongioseum tissue that is found in the interior of the vertebrae. The harder cortical bone tissue provides sufficient strength to transmit the biomechanical forces exerted on the spinal column to the implant. The wide bearing surfaces or contact surfaces of the implant can withstand the biomechanical forces and inhibit subsidence of the implant into the vertebral bodies. This provides an implant that can safely and durably support the spinal column during normal and/or recommended patient activity.

The longitudinal walls of the implant can be narrow in a cross-sectional dimension, measured transverse to the longitudinal axis. The implant can be fabricated to minimize the thickness of the longitudinal walls, yet still provide requisite compressive strength to maintain desired disc space height and orientation. This provides an implant having an enlarged cavity compared to implant having thicker longitudinal walls. The larger cavity is capable of receiving a greater amount of osteogenic material. This, in turn, provides increased success rate for spinal fusion and ultimately provides a stronger more stable bone bridge between the adjacent vertebrae.

Since the wide, edge contact or bearing surface of the implant supports the majority of the biochemical forces exerted by the spinal column, it is possible to remove a portion of the cortical tissue from the endplates of the vertebra to reveal the cancelleous bone tissue or spongioseum tissue without adversely affecting the load bearing capability of the endplates. The implant can be placed within the disc space and provide intimate contact of the osteogenic material within the cavity and the exposed bone tissue of the opposing vertebrae. This provides the advantages of promoting arthrodesis of the vertebrae.

Further, an integral implant design can be provided with minimal or no projections or protrusions extending from its exterior surfaces. In one embodiment, the outer surfaces of the endwalls are provided with a rounded shape or rounded-over edges. Additionally, the edges where the longitudinal walls meet the upper and lower surfaces can be chamfered, beveled or rounded. These edges provide advantages in that the resulting implant can be simply installed into the prepared disc space without danger of any projections, quarters, edges or the like tearing or gouging the surrounding tissue and therefore minimizes unintentional injuries to the adjacent tissue.

The implant has an interior cavity to serve as a depot for osteogenic material. It is desirable to provide a large internal cavity to obtain a large bone bridge or new bone growth between the adjacent vertebrae. In one form the cavity can be provided to have a shape that generally corresponds to that of the external surface of the implant. Thus in one form, the basic interior shape of the cavity is also a box-shaped and its dimensions are similar to that of the outer dimensions of the body. Alternatively, the cavity has a height that varies along the longitudinal axis. For wedge shaped implants, the internal dimensions of the cavity can also provide a wedge shaped hollow interior. Similarly, when the exterior profile of the implant is generally lens-shaped the interior chamber can be lens-shaped as well. The interior cavity can be made larger in the present invention by decreasing the thickness of either or both of the longitudinal walls and the upper and lower surface walls. This can be accomplished by providing the endwalls of substantial thickness to support the biomechanical stress exerted by the spinal column. In another form, the height of the cavity is substantially consistent along the longitudinal direction to facilitate uniform loading of an osteogenic material in the cavity. In still another form, the cross-sectional area of the cavity, measured in a plane lying substantially transverse to the longitudinal walls is equal to or greater than the cross-sectional area of either of the openings in the upper and lower surfaces of the implant.

The implant can also be provided efficiently, economically and readily mass produced while maintaining high quality assurance over very specific tolerances for the outside dimensions, and compressive and elastic moduli. The number of steps necessary for the production of the implant are significantly reduced—particularly the machining processes and milling procedures are reduced. The compact design of the implant often makes it possible to provide the implant body in a variety of materials including metallic materials, synthetic materials, polymeric materials, ceramic materials, and composite materials including reinforced materials i.e. glass, fiber, and/or carbon fiber reinforced materials (CFRP). These preferred materials for fabricating implants in the present invention reduce costs, increase service life and provide excellent physiological compatibility. The material can be selected to be either a substantially permanent material, a biodegradable material or a bioerodable material. Further, the implant material can be provided to be radio-opaque to facilitate monitoring of bone ingrowth both into the implant and between the opposing endplates of the adjacent vertebrae.

The basis body includes at least one groove. Preferably at least one groove is formed on each of the cross-wise extending surfaces of the endwalls. The groove can extend transverse across the entire width direction of the implant body. The groove can be readily formed as an integral feature on the implant body. The groove can provide sufficient resistance to expulsion and/or migration in the disc space. Further, the groove does not obstruct impaction of the implant into the disc space. The groove including its upper edges lies either coplanar with, or below the exterior surface (s) of the implant and extends inwardly. After implantation of the implant into the prepared disc space, the implant can be maintained in the desired position by the pressure exerted on it by the spinal column. Tissue is forced into the grooves. The bone material fills the grooves of the implant and helps secure the implant's position in the disc space. The grooves can also engage bony tissue proximal to the apophyseal ring under the compressive biomechanical force exerted by the spinal column on the contact surfaces of the implant.

Additionally, the outer surface of the implant can, but is not required to include anti-expulsion structures or features. Such features include ridges and the like. These features can be provided either through a milling and/or machining process or through the molding of the implant. The anti-expulsion features inhibit rejection of the implant from the disc space and/or inhibit undesirable migration within the disc space. The outer surface of the implant as a whole can be roughened, by which the surrounding tissue interengages or mechanically interlocks the roughened outer surface of the implant.

The longitudinal walls of the implant are preferably formed to be substantially planar and parallel to each other. This provides significant advantages regarding the installations of the implant into the disc space as will be discussed. The thickness of the longitudinal walls can be selected to be substantially less than the thickness of the endwalls. For example the thickness of the longitudinal walls measured transverse to the longitudinal axis can be about one-half the thickness of the endwalls measured substantially parallel to the longitudinal axis. More preferably the thickness of the longitudinal walls is between about 0.5 and 0.4 times as thick as the thickness of the endwalls. The ratio of the thickness of the other longitudinal walls to the endwalls provides an implant having an ample interior cavity to receive the osteogenic material and yet provides an implant that is able to support the mechanical load exerted from the spinal column.

In selected the embodiments, the implant can be provided to have a generally convex shape. This can be accomplished by providing the longitudinal walls with upper and lower edges having a convex shape. The upper and lower surfaces of the longitudinal walls can have a maximum height that is positioned between the first and second endwalls. In one form, the convex surface portion can be provided to engage in the natural concavity surface portions of the opposing endplates. This shape has the advantage that the implant can be readily fitted to the respective vertebral endplates without any previous machining or cutting process on the endplates. It will be understood that the endplates of the adjacent vertebrae can be cut or shaved to precisely match the geometry of the implant.

In other embodiments the longitudinal walls define a lordotic profile. In this configuration the longitudinal walls are shaped to provide an implant that conforms to the desired lordosis or natural curvature of the spine.

Both the upper and lower surfaces define openings into the inner cavity. These openings ensure that the osteogenic material in the internal cavity contacts the bone tissue in the opposing vertebral endplates. Preferably the upper and lower surfaces provide an opening that is substantially the same or equivalent to the cross-sectional area of the internal cavity. This provides the greatest amount of contact between the included osteogenic material and the opposing endplates.

Preferably an opening is formed in each of the two longitudinal walls to provide access to the interior cavity. This also allows blood and nutrients to infuse laterally into the cavity containing an osteogenic material. Further, the lateral openings allow the osteogenic material to enhance bone growth around the implant between pairs of adjacent implants in the disc space and to facilitate spine fusion from all sides, laterally and vertically. In preferred embodiments the longitudinal walls each have at least one large opening into the interior cavity. It is understood that a plurality of smaller openings each opening providing access to the interior chamber can also be formed in the longitudinal walls. Preferably each of the small openings has a diameter, which in comparison with the height of the longitudinal walls, is small. Preferably a maximum of two large through holes are formed to each of the longitudinal walls. The diameter of each of the two large through holes corresponds approximately to half of the height of the longitudinal walls.

The implant body preferably includes on its rear endwall, a tool-engaging portion, for example provided on an end of an implant holder. Preferably the tool-engaging portion comprises an outwardly opening or a bore formed in the middle of the rear endwall of the body. The opening can, but is not required to, include a threaded interior to receive a correspondingly threaded pin or stud on the tool. The tool-engaging portion can also include a pair of opposing grooves formed laterally beside the opening. The opening is positioned in line with the laterally extended grooves. In preferred forms, the rear wall is substantially free of any further projections and or shoulders. The counterpart portions on the tool can also include a mid-position pin as well as outwardly extending blades to engage the laterally grooves formed in the endwall of the implant. The pin can engage within the opening in the endwall and can be used to fixedly secure the implant to the tool and facilitate alignment of the implant during insertion. Alternatively, the tool can include a pair of opposing arms that can open and close to clamp or grip the implant either along a portion of the opposing longitudinal walls or along the upper and lower surfaces. Preferably the tool engaging portion is formed such that the implant can be tightly attached to the tool in a relatively simple manner so that the tool can be used both as implant holding tool as well as on impacting tool to insert the implant into the disc space.

The vertebral implant according to the present invention preferably is provided with the following mechanical properties:

static compressive resistance in height direction, transverse to the longitudinal axis: greater than or equal to about 15,000N fatigue strength corresponding to this compressive resistance: greater than or equal to about 5,000 N torsional resistance (torque in(around) longitudinal direction of the implant: greater than or equal to about 4 Nm, In other embodiments, the implants according to the present invention exhibit a compressive strength that corresponds to the strength of the healthy bone tissue around the site wherein the implant is to be placed.

The above-described implants can be prepared of a wide variety of materials including metallic materials, synthetic, organic materials, composites, ceramic, and metal. Preferably the implants are formed of a synthetic, non-metallic material. The implants of the present invention can be either essentially permanent implants, which do not readily biodegrade. These implants can remain in the intervertebral space and often are incorporated into the bony tissue. Alternatively, the implant can biodegrade and can be substantially replaced by bone tissue.

Examples of non-biodegradable polymeric or oligomeric materials include the, polyacrylates, polyethers, polyketones, polyurethanes, and copolymers, alloys and blends thereof. Use of the term co-polymers is intended to include within the scope of the invention polymers formed of two or more unique monomeric repeating units. Such co-polymers can include random copolymers, graft copolymers, block copolymers, radial block, diblock, triblock copolymers, alternating co-polymers, and periodic co-polymers. Specific examples of non-biodegradable polymeric materials include: poly(vinyl chloride) (PVC); poly(methyl (meth) acrylate); acrylics; polyamides; polycarbonates; polyesters; polyethylene terephthalate; polysulfones; polyolefins, i.e. polyethylene, polypropylene, and UHMWPE (ultra high molecular weight polyethylene); polyurethane; polyethers, i.e., epoxides; poly(ether ketones) (PEK), poly(ether ether ketones) (PEEK), poly(aryl ether ketones) (PAEK), and poly(ether ether ketone ether ketone) (PEEKEK). A wide variety of suitable poly(ether-co-ketone) materials are commercially available.

Alternatively, implants of this invention can be made of a material that either biodegrades or is bioabsorbed. Typically, biodegradable material is a polymeric material or oligomeric material and often the monomers are joined via an amide linkage such as is observed in poly(amino acids). When the implant is formed of material that biodegrades, it is desirable to provide a biodegradable material that degrades at a rate comparable to the bony ingrowth characteristic of bone fusion—often referred to as creeping substitution. It is still more preferred to select the biodegradable material to remain in situ and capable of providing sufficient biomechanical support for the spine even after a bone bridge has grown and formed through the through-holes of the implant. Selecting an appropriate synthetic material can vary the biodegradation rate of the implant. The degradation rate of the selected material can be further modified, for example, increasing the degree of polymerization and/or increasing the amount of crosslinking between the polymer chains can decrease the degradation rate. Further, it is not intended to limit the preferred materials to substances that are partly or totally reabsorbed within the body. Rather substances that can be broken down and eventually flushed from the body are also intended to come within the scope of this invention.

Examples of biodegradable polymers for use with this invention include poly(amino acids), polyanhydrides, polycaprolactones, polyorthoesters polylactic acid, poly(lactide-co-glycolide), i.e., copolymers of lactic acid and glycolic acid, including either D, L and D/L isomers of these components. One example of a preferred biodegradable polymer for use with this invention is a copolymer of 70:30 poly(L, DL) lactate commercially available from Boehringer Ingelheim.

A particularly advantageous benefit provided by this invention is the ease of manufacturing suitable synthetic implant. Implants formed of polymeric, oligomeric and composite material can be manufactured using known fabricating techniques, including extrusion, injection and blow molding processes. In addition, selected polymeric materials are provided by suppliers in a form that can readily formed, and/or molded, usually at an elevated temperature. A copolymer of D/L lactate is one specific example. This material can be obtained in a wide variety of forms including pellets, granules, sheets, or ingots. The material can be molded at a temperature of about 55° C. or higher to provide a desired shaped and sized implant. The material can be repeatedly heated and contoured without any significant change in its material or chemical properties. In addition, material is readily cut using an electro-cautery to readily shape the implant to the configuration of the bone surfaces. The polymeric, oligomeric and composite materials permit use of lower cautery temperatures to cut or shape the implant immediately before or during the operation.

Examples of metallic materials include any of the metals and metals alloys known to be suitable for implant in animals, including humans. Specific examples include titanium, titanium alloys, and surgical implant grade steel.

Specific examples of ceramic materials for use with this invention include glass, calcium phosphate, alumina, zirconia, apatite, hydroxyapatite and mixtures of these materials.

Composites are also useful with this invention. Composites can combine two or more of the desired materials to form an implant body for implantation. Examples of composites include reinforced ceramic, glass or polymeric materials. Preferred composites include a fiber-reinforced material such as a glass or carbon fiber reinforced organic polymer.

Carbon fiber vertebral implant of this invention can be prepared according to the following method. A fiber composite material such as a glass or a carbon fiber composite material (GFRP or CFRP, respectively) is first soaked with a liquid plastic, in particular a resin material such as epoxy resin. The soaked fibers are wound around the winding mandrel as bunched fibers, in particular, using a filament winding method. Subsequently the plastic is cured; this is best done by a controlled temperature treatment. The winding mandrel is advantageously formed to have a simple rod-like shape, and, consequently, the resulting elongated basis body provided with a cavity having dimensions and configuration corresponding to the exterior configuration of the winding mandrel. Since the end measurements of the cavity are already formed by the winding mandrel, little if any machining is required on the inner surfaces of the limiting walls surrounding the cavity. The soaked fiber material is wound around the winding mandrel until the resulting body has external dimensions that are about the same or slightly smaller than the desired final dimensions. Preferably the soaked fibers are wound about the mandrel until the resulting body has reached at least a selected minimum wall thickness for the thickest wall, i.e., the endwalls to minimize subsequent machining steps.

The wound implant body is machined according to following steps. The winding mandrel is replaced with a receiving mandrel to center the basis body into a chucking device for accurate machining. The exterior of the basis body is machined to an intermediate configuration that has exterior dimensions smaller than the desired final dimensions. Preferably, each surface of the intermediate configuration is smaller than the final configuration by approximately the same amount. That is, the basis body is machined to have an intermediate configuration that substantially corresponds to the final configuration, only as a scaled down version. The intermediate configuration is a scaled down version so that as little material as possible needs to be machined during the final machining step. Preferably, the winding/machining steps provide an intermediate implant that has external dimensions of about 90–98%, more preferably 95%, of the outer measurements of the final basis body.

It should be understood that since in the final configuration some walls are thicker than other walls, the basis body is not to be wound to have the final measurements on every exterior surface. Selected surfaces require that additional plastic material be wound about to the mandrel. Milling, grinding and/or polishing methods are possible methods of machining. During the prior machining steps, the different wall thickness of the longitudinal and the frontal walls are preset into the implant body by corresponding machining from the selected outer sides of the basis body.

In the next step, the winding mandrel is re-inserted and additional fibrous/resin material is wound about the basis body. As before, the fibers are soaked with resin. The coated fibers are wound around the machined, intermediate basis body to build the sides to the desired thickness. The coated fibers are wound about the basis body until it approaches the desired exterior dimensions. That is, fiber and resin material are wound around the basis body until the exterior dimensions are at least a great as the desired exterior measurements of final implant. In this step the basis body is reaches its final outer dimensions. In preferred embodiments, the fibers and resin are the same as used in the first winding step.

This method provides a closed course of fibers at both the inner and outer surfaces of the implant, and taking full advantage of the strength increasing properties of the fiber material. A completely closed, unadulterated course of fibers is achieved at the inner surfaces defining the cavity, since these surfaces are not machined after the winding process. Since two winding steps are use to fabricate the basis body, only a little amount of material remains to be removed from the basis body after the second machining step. In this final machining step very few, if any, of the fibers in the outer fiber winding are cut. The integrity of the fiber windings is maintained largely intact.

Optionally, the basis body is provided with holes and grooves by corresponding machining steps after the second winding procedure and after the plastic has been cured. In the vertebral implant according to the present invention these are the through holes in the longitudinal and frontal walls as well as the grooves of the receiving means and the grooves in the crosswise extending free edge surfaces of the frontal walls.

This method provides a highly stable vertebral implant from fiber-reinforced material at low costs. In addition, the fibers can be orientated to wind in a single direction or optionally in varying directions.

Alternatively, the implant formed of a fiber composite material can be prepared using a pultrusion method by saturating individual fibers or bundles of fibers with a resin, for example one the polymeric materials previously described, and pulling the resin saturated fibers through a die to provide the profile of the desired implant. The resulting implant can be machined as described above to provide the final configuration including a threaded exterior, chamfer surfaces and openings. Implants prepared according the pultrusion method generally have fibers orientated in the same direction, for example either in an axial direction or longitudinal direction.

In yet another method the fiber reinforced composite can be prepared using chopped fibers (or short fibers) that have been embedded within a curable resin, for example one or more of the polymers described above. The chopped fiber reinforced material can be cured, molded and/or extruded according to techniques known in the art.

The osteogenic compositions used in this invention can be harvested from other locations in the patient, for example from the cancelleous bone in the vertebrae or from other bone structures, such as the iliac crest. In other embodiments, the osteogenic material can comprise a therapeutically effective amount of a bone morphogenetic protein in a pharmaceutically acceptable carrier. The preferred osteoinductive factors include, but are not limited to, TGF B family of glycoproteins, the recombinant human bone morphogenic proteins (rhBMPs) because they are available in unlimited supply and do not transmit infectious diseases. Most preferably, the bone morphogenetic protein is a rhBMP-2, rhBMP-4, rhPMB-7 or heterodimers thereof. The concentration of rhBMP-2 is generally between about 0.4 mg/ml to about 1.5 mg/ml, preferably near 1.5 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenic protein from bone are described in U.S. Pat. No. 4,294,753 to Urist and Urist et al., 81 PNAS 371, 1984.

The choice of carrier material for the osteogenic material is based on the application desired, biocompatibility, biodegradability, and interface properties. The bone growth inducing composition can be introduced into the pores of the bone material in any suitable manner. For example, the composition may be injected into the implant cavity. The osteogenic factor, preferably a BMP, may be provided in freeze-dried form and reconstituted in a pharmaceutically acceptable liquid or gel carrier such as sterile water, physiological saline or any other suitable carrier. The carrier may be any suitable medium capable of delivering the proteins to the implant. Preferably the medium is supplemented with a buffer solution as is known in the art. In one specific embodiment of the invention, rhBMP-2 is suspended or admixed in a carrier, such as, water, saline, liquid collagen or injectable bicalcium phosphate. In a most preferred embodiment, BMP is applied to the pores of the graft and then lypholized or freeze-dried. The graft-BMP composition can then be frozen for storage and transport. Alternatively, the osteoinductive protein can be added at the time of surgery.

Other osteoinductive protein carriers are available to deliver proteins. Potential carriers include calcium sulfates, polylactic acids, polyanhydrides, collagen, calcium phosphates, polymeric acrylic esters and demineralized bone. The carrier may be any suitable carrier capable of delivering the proteins. Most preferably, the carrier is capable of being eventually resorbed into the body. One preferred carrier is an absorbable collagen sponge marketed by Integra Life-Sciences Corporation under the trade name Helistat®

Absorbable Collagen Hemostatic Agent. Another preferred carrier is an open cell polylactic acid polymer (OPLA). Other potential matrices for the compositions may be biodegradable and chemically defined calcium sulfates, calcium phosphates such as tricalcium phosphate (TCP) and hydroxyapatite (HA) and including injectable bicalcium phosphates (BCP), and polyanhydrides. Other potential materials are biodegradable and biologically derived, such as bone or dermal collagen. Further matrices are comprised of pure proteins, extracellular matrix components or a mixture of biological components and synthetic materials, e.g., proteins and/or amino acids embedded in plastics or ceramics. The osteoinductive material may also be an admixture of BMP and a polymeric acrylic ester carrier, such as polymethylmethacrylic.

One carrier is a biphasic calcium phosphate ceramic. Hydroxyapatite/tricalcium phosphate ceramics are preferred because of their desirable bioactive properties and degradation rates in vivo. The preferred ratio of hydroxyapatite to tricalcium phosphate is between about 1:99 and about 65:35. Any size or shape ceramic carrier, which will fit into the cavity defined in the implant is contemplated. Ceramic blocks are commercially available from Sofamor Danek Group, B. P. 4–62180 Rang-du-Fliers, France and Bioland, 132 Route d: Espagne, 31100 Toulouse, France. Of course, rectangular and other suitable shapes are contemplated. The osteoinductive factor is introduced into the carrier in any suitable manner. For example, the carrier may be soaked in a solution containing the factor.

In order to prevent a sliding of the hand tool off the implant, the receiving means on the rear wall is advantageously formed such that it also serves as a holding means. The hand tool, can for instance, be provided with a clamp, by means of which the implant can be held tight, e.g. by engagement into the grooves, so that the implant is connected with the hand tool as a joined unit and can be readily manipulated by the surgeon to precisely place the implant in the desired position in the disc space. In order to determine the position of the implant with respect to the hand tool even more precisely, the opening in the implant can extend through the rear wall and aligned with a second through hole formed through the opposite frontal wall on the opposite end of the implant. A corresponding pin or shaft on the hand tool can be extended through the first through hole and into the second though hole thereby centering the implant on the hand tool. The frontal side through hole enhances access to the implant cavity to facilitate ingrowth of tissue into the implant from its front side.

The intervertebral implant according to the present invention can be implanted into prepared disc space from a variety of orientations or directions including posteriorly, posterior-laterally, anteriorly, and anterior-laterally. The disc space is prepared prior to implantation of the space. The typically partial or full discectomy is performed. The endplates are preferentially cut to expose the cancelleous bony tissue. Preferably only portions of the endplates that will be directly opposite the openings in the implanted implants are cut or scraped to expose the underlying cancelleous bone tissue. This preserves as much integrity of the endplates as possible to minimize the implanted implant's subsidence into the endplate tissue. (Scrapers/chisels suitable for use in this invention are discussed in U.S. patent application Ser. No. 09/420,622 entitled "Spinal Implant Method and Cutting Tool Preparation Accessory For Mounting the Implant" filed on Oct. 10, 1999, which is incorporated by reference in its entirety.) The upper and lower surfaces of each of the longitudinal walls can engage the uncut portions of the endplates while the bearing surfaces of the implant bear against the thicker cortical bone tissue on the apophyseal ring. The preparation can, but is not required to, include cutting the cortical bone in the endplates to provide an opening into the interior of the disc space, as well as, cutting or removing portions of the cortical bone tissue of the endplates to expose the cancelleous bone tissue. More preferably, the implant is inserted into the disc space without trimming portions of the cortical rim. If needed, the vertebrae are distracted to provide sufficient clearance between the opposing cortical rims of the adjacent vertebrae for insertion of the implants. Thereafter the intervertebral implant is inserted into the prepared disc space such that the upper and lower surfaces contact the respective opposing endplates while the openings in the upper and lower surfaces are opposite the cut portions of the endplates. The bearing surfaces are adjacent to the interior surfaces of the cortical rim around the vertebral bodies known as the apophyseal ring. After the implants have been inserted in the disc space, if needed or desired, the vertebral bodies can be compressed toward each other to decrease the disc space. The disc space compression can embed one or more of the implant's surfaces into the cortical bone of the endplate. In one embodiment, the upper and lower surfaces of the implant are embedded in the previously uncut portions of the endplate. Additionally pedicle screws, plates and/or spinal rods or any other known fixation devices and techniques can be used to maintain disc space separation and spinal orientation.

The present invention contemplates modifications as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

BEST MODE FOR CARRYING OUT THE INVENTION

Figure 1:
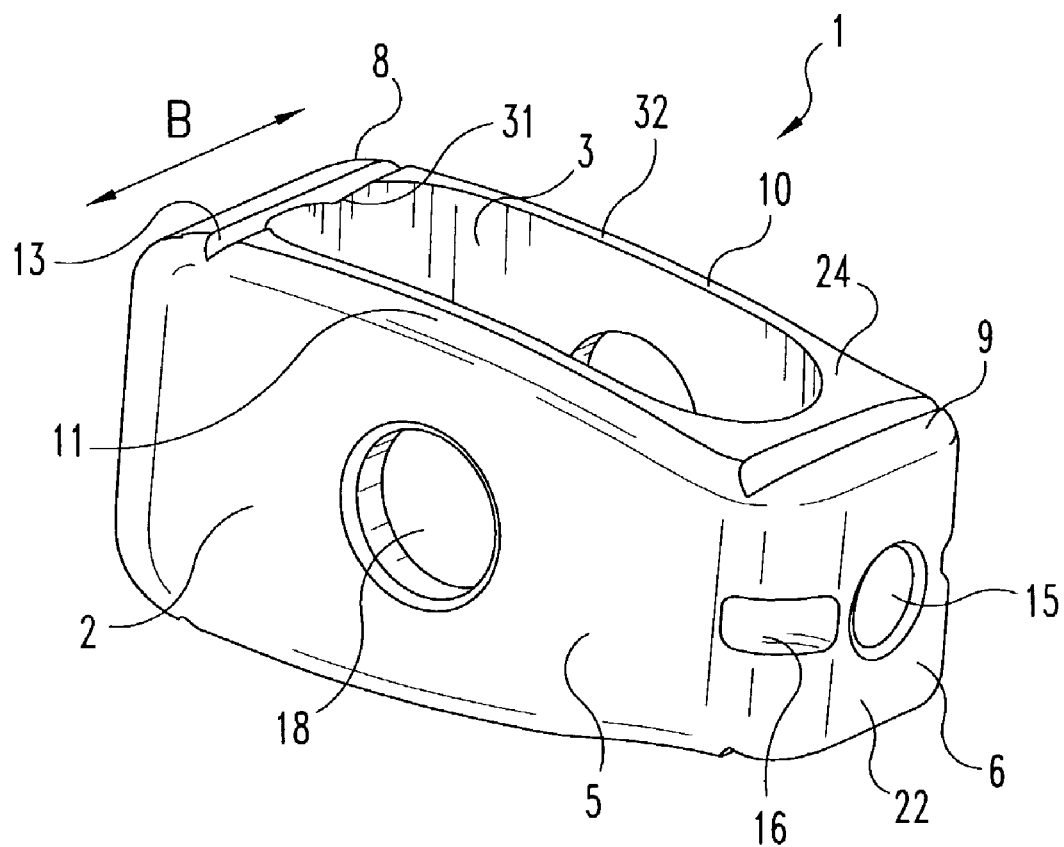
FIG. 1 is perspective view of one embodiment of an intervertebral implant according to the present invention.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

FIGS. 1–5 illustrate intervertebral implant 1 according to the present invention. Implant 1 is formed by an elongated basis body 2 defining a longitudinal axis. Cavity 3 is formed in body 2. Cavity 3 is surrounded by two longitudinal walls 4, 5 and two endwalls 6, 7 (rear wall 6 and a front wall 7). Cavity 3 is formed to extend through in the height direction H of the body 2 and is provided to have in a plan projection the shape of an elongated rectangle with semi-circles being flushly added at its frontal sides. The cavity 3 has the same plan projection throughout the entire height of the implant and consequently is formed in the basis body 2 without any undercut regions. In a preferred embodiment, the endwalls 6, 7 are, throughout their respective entire wall surface, formed to be thicker than the longitudinal walls 4, 5. In the illustrated embodiment, the walls 6, 7 are provided to have approximately 2.5 times the thickness of the longitudinal limiting walls 4, 5 about cavity 3; measured at the respective center of the walls.

Body 2 comprises bearing surfaces 8, 8', 9, and 9' formed by the cross-edge surfaces of the endwalls 6, 7, which edge surfaces 8, 8', 9, and 9' have a larger width than the respective cross-edge surfaces 10 and 11 formed by the transverse edge surfaces of the longitudinal walls 4, 5.

The surfaces 8, 8', 9, and 9' extend in a continuous way and such that they are substantially smooth surfaces, free of steps and protrusions. As is evident from FIG. 13, surfaces 8, 8', 9, 9' serve as contact and/or support surfaces to the vertebral bodies $W^2$ and $W^3$ and support a substantial component of the compressive forces occurring between the adjacent vertebrae $W^2$ and $W^3$. For this, the fact that the vertebral bodies $W^{1,2}$ comprise a harder, cortical bone material K in their outer regions, near the cortical rim structure whereas a softer, cancelleous or spongiose bone material, S, exists inside the vertebral bodies $W^{1,2}$, is taken advantage of. Herein, the circumferential shell or cortical rim of the vertebral bone $W^{1,2}$ consisting of a cortical bony tissue and to which the walls 6, 7 of the implant 1 are applied via the bearing surfaces 8, 8', 9, 9' is sufficiently stable to take up the compressive force along the longitudinal direction of the spinal column and to transmit the compressive force to the implant 1 proximate to bearing surfaces 8, 8', 9, 9'.

Figure 2:
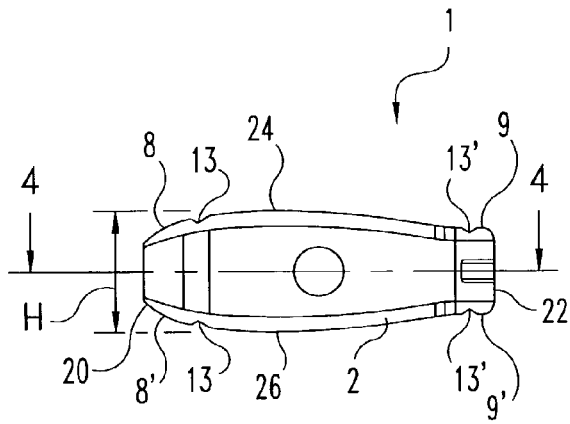
FIG. 2 is an elevated side view of the implant of FIG. 1.
Figure 3:
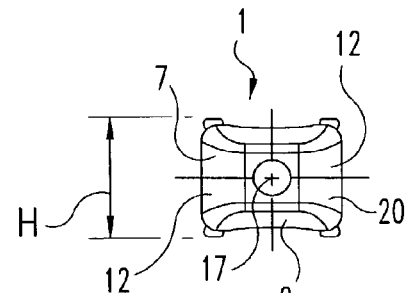
FIG. 3 is an elevated end view of the intervertebral implant of FIG. 1.
Figure 6:
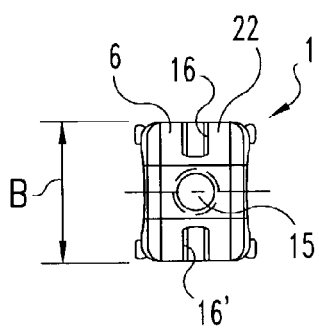
FIG. 6 is an elevated second end view of the intervertebral implant of FIG. 1.

Additionally, FIG. 2 illustrates body 2, viewed in its widthwise lateral direction B, i.e. perpendicular to the bearing surfaces 8, 8', 9, 9'. Upper surface 24 and lower surface 26 have a bi-convex shape in the longitudinal direction with a maximum height H provided between first end 20 and second end 22. In the illustrated embodiment, the maximum height H of body 2 is located proximate to the front edge 31 of opening 32 in upper surface 24. (See FIG. 1.) The resulting lens-shaped design of the body 2 allows it to be placed inside the disc space and restore and/or maintain a desired disc space height. This configuration maintains upper and lower surfaces 24, and 26 in contact with the vertebrae. Consequently the osteogenic material in cavity 3 is pressed against the cancellous or spongioseum bone tissue of the vertebrae and facilitates arthrodesis. Additionally since body 2 matingly engages with the natural concavity of the endplates, the potential for retropulsion is minimized.

Figure 4:
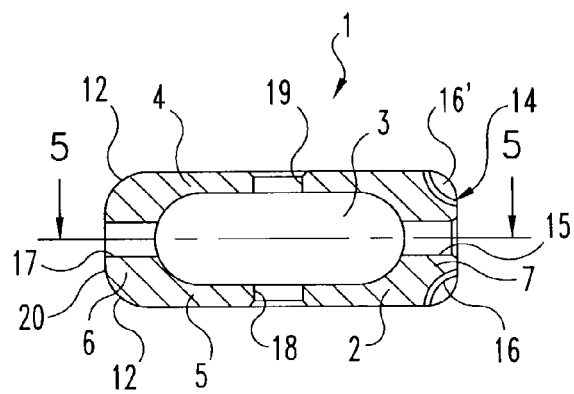
FIG. 4 is a cross-sectional view of the intervertebral implant of FIG. 1 taking along intersection line designated 4—4 in FIG. 2.
Figure 5:
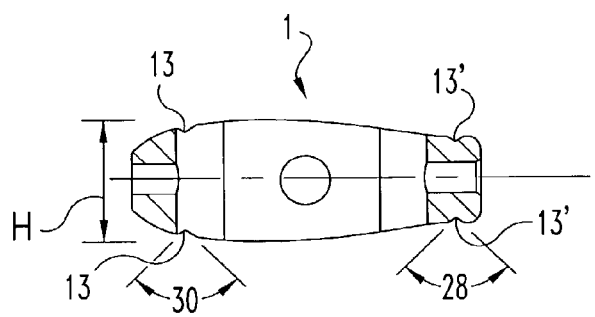
FIG. 5 is a cross-sectional view of the intervertebral implant of FIG. 1 taken along intersection line designated 5—5 in FIG. 4.

FIG. 4 is a cross-sectional view along intersection line 4—4. Implant 1 is provided as a substantially elongate rectangle having substantially planar longitudinal walls. Corners 12 on first end 20 of this rectangular shape are rounded to provide body 2 with a generally tapered profile on first end 20. Corners 12 have radii of about ⅓ of the width of the implant 1. As can be observed from FIGS. 1 and 3, the longitudinal and frontal edges of the implant 1 are rounded resulting in a streamlined front face to ease insertion of implant 1 into the disc space. Consequently, implant 1 can be inserted into disc space, with minimal risk of unintended tissue injury.

In an alternative embodiment the peripheral edge of the opening 32 defines an acute angle or a sharp edge about cavity 3. This sharp edge poses minimal risk of tissue injury during installing the implant exists. In contrast to the longitudinal and frontal implant edges, peripheral edge of opening 32 is located further inwards towards the central longitudinal axis because the overall lens-shape of the implant 1 tapers from a maximum height proximate to front edge 31 of opening 32 to a smaller height proximate to second end 22. Bearing surfaces 9 and 9' of which, if viewed in the lateral direction of the implant 1, extend almost parallel to the longitudinal central axis of the implant 1.

Grooves 13 and 13' extend transverse to the longitudinal axis in the widthwise direction B of the implant 1. Grooves 13 and 13' are formed in each of the contact surfaces 8, 8', 9, and 9'. Grooves 13 and 13' are provided to be a triangular groove or trough, the side flanks of which form an angle 28 and 30 of about 90° with respect to each other; however, other shapes for the groove, such as a rectangular or a U-shape are also possible. The compressive pressure forces from the two vertebrae, W, press tissue into grooves 13 and 13' and provide additional anchoring of the implant 1 in the disc space.

A receiving means 14 for a hand or an operation tool is provided at the rear end of the basis body 2 (depicted as the right end of implant 1 in FIGS. 1, 2, 4, 5 and 7). The receiving means 14 comprises a through hole 15 formed in the middle of the rear wall 7. Through hole 15 can be provided to engage a corresponding projection on the hand tool. Grooves 16 and 16' in second end 22 extend laterally in the horizontal plane to engage in blades on the hand tool.

A second through hole 17 aligned to the hole 15 is formed in the middle of the first end 20 of the basis body 2. A corresponding counterpart pen extension or stud of the hand tool can engage into (and through) through hole 17 for centering the implant 1 with respect to the tool. The through hole 17 and the hole 15 subsequently enable growth of bone material into the implant from the front and rear sides.

Two apertures 18 and 19 are formed in each of the longitudinal walls 4 and 5 of the cavity 3 in the embodiment according to FIG. 1. In alternative embodiments, two or more openings are formed in each longitudinal wall 4 and 5. The diameter of each of the through holes 18 and 19 corresponds to about half of the maximum height H of implant 1. Bone material can grow in a lateral direction into through holes 18, 19 to anchor implant 1 in the disc space.

Figure 7:
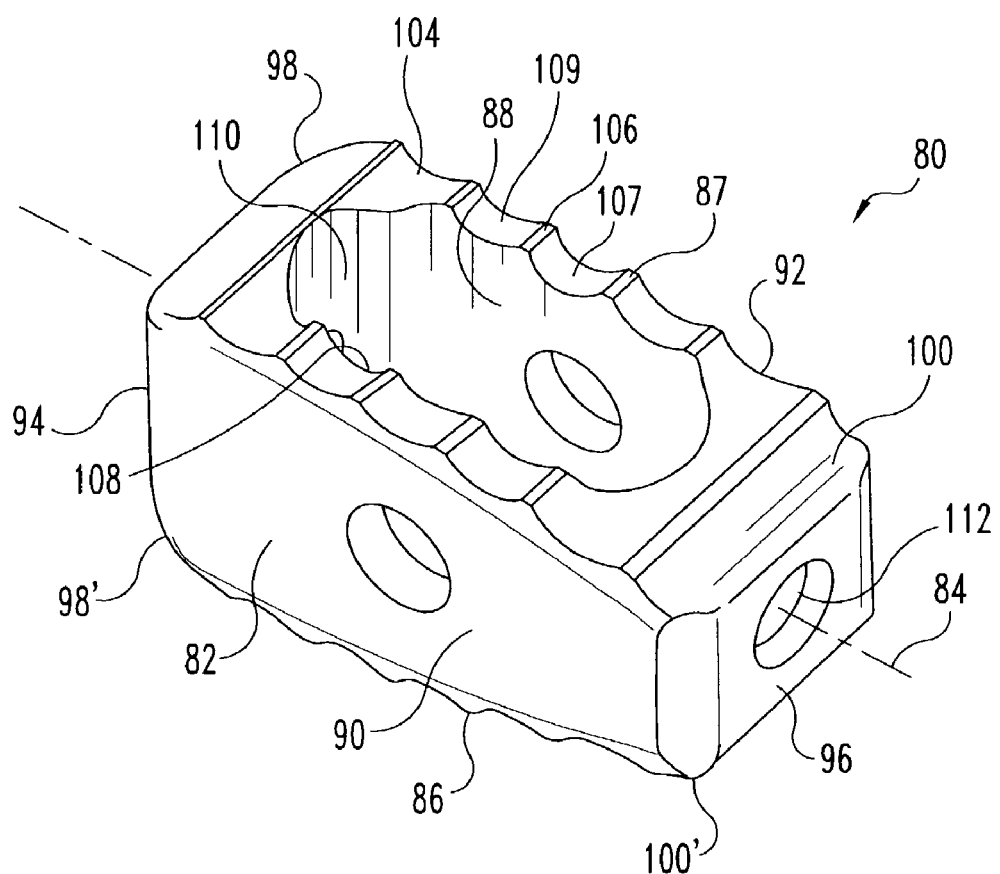
FIG. 7 is a perspective view of an alternative embodiment of an implant according to the present invention.

FIG. 7 is a perspective view of another embodiment of an implant 80 for use in the present invention. Implant 80, similar to implant 1, comprises an elongate basis body 82 defining a longitudinal axis 84. Basis body 82 has a generally bi-convex or lens-shape profile defined by lower surface 86 and upper surface 87. Upper and lower surfaces 86 and 87 have a plurality of grooves 104 formed therein. Additionally, basis body 82 includes an internal cavity 88 surrounded by first and second longitudinal walls 90 and 92, respectively, and endwalls 94 and 96. Endwalls 94 and 96 each have a thickness measured generally along the longitudinal axis that is greater than the thickness of either first or second longitudinal wall 90, 92. Further endwalls 94 and 96 each include cross-edge surfaces defining bearing surfaces 98, 98', 100, and 100'.

A plurality of grooves 104 extend across bearing surfaces 98, 98' 100 and 100'. Additionally, but not required, selected grooves can extend across upper and lower surfaces 86 and 87 orthogonal to longitudinal axis. The selected grooves are interrupted by the peripheral edge 108 of opening 110 into cavity 88. Otherwise grooves 104 extend laterally across basis body 82 from longitudinal wall 90 to longitudinal wall 92. Grooves 104 can be provided as swales cut in to lower and upper surfaces 86 and 87. Additionally grooves 104 define a uniform curvature cut in to the upper and lower surfaces 86 and 87. In one form grooves 104 are not symmetrical. Grooves 104 can be shallow troughs and can be substantially wider than they are deep.

In the illustrated embodiment, adjacent grooves 107 and 109 are separated by a land 106. Land 106 is provided to be substantially co-planar with the upper surface 86 and lower surface 87.

Basis body 80 also includes a smooth bore 112 formed in endwall 96. Smooth bore 112 can be used to locate an insertion instrument prior to grasping longitudinal walls 90 and 92.

Figure 8:
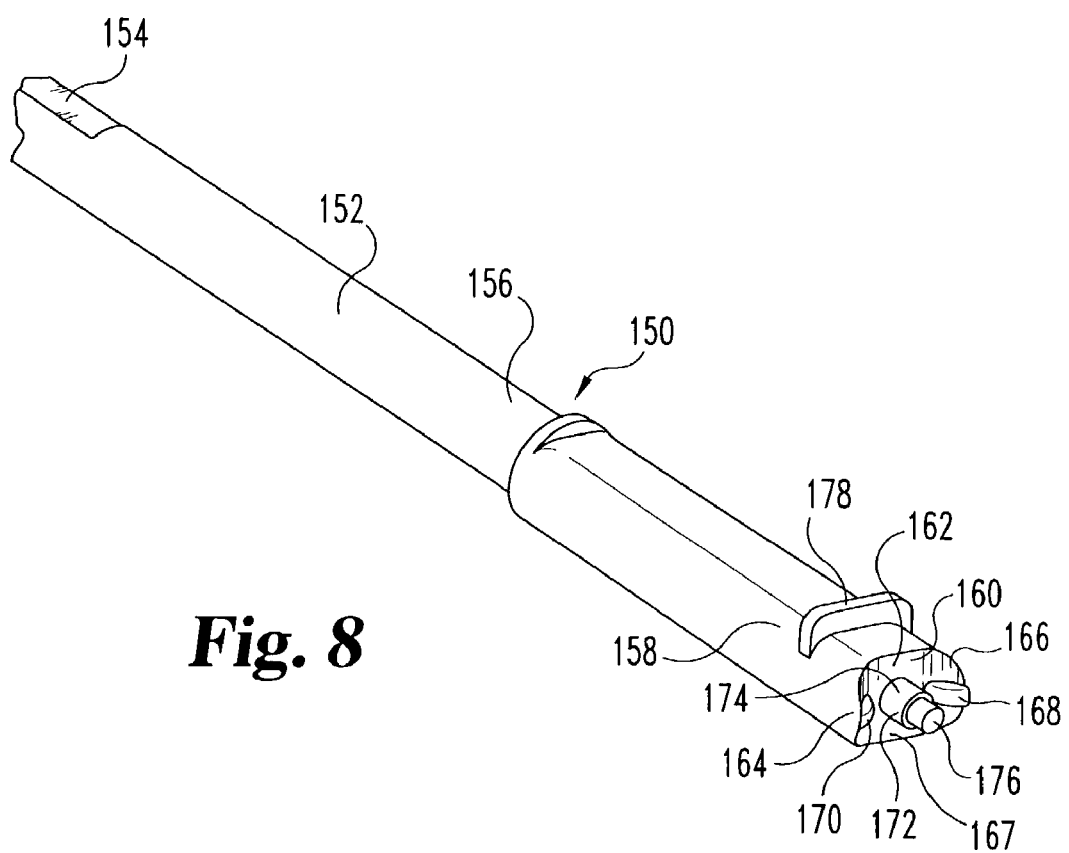
FIG. 8 is a perspective view of an implant holder for use with the present invention.
Figure 9:
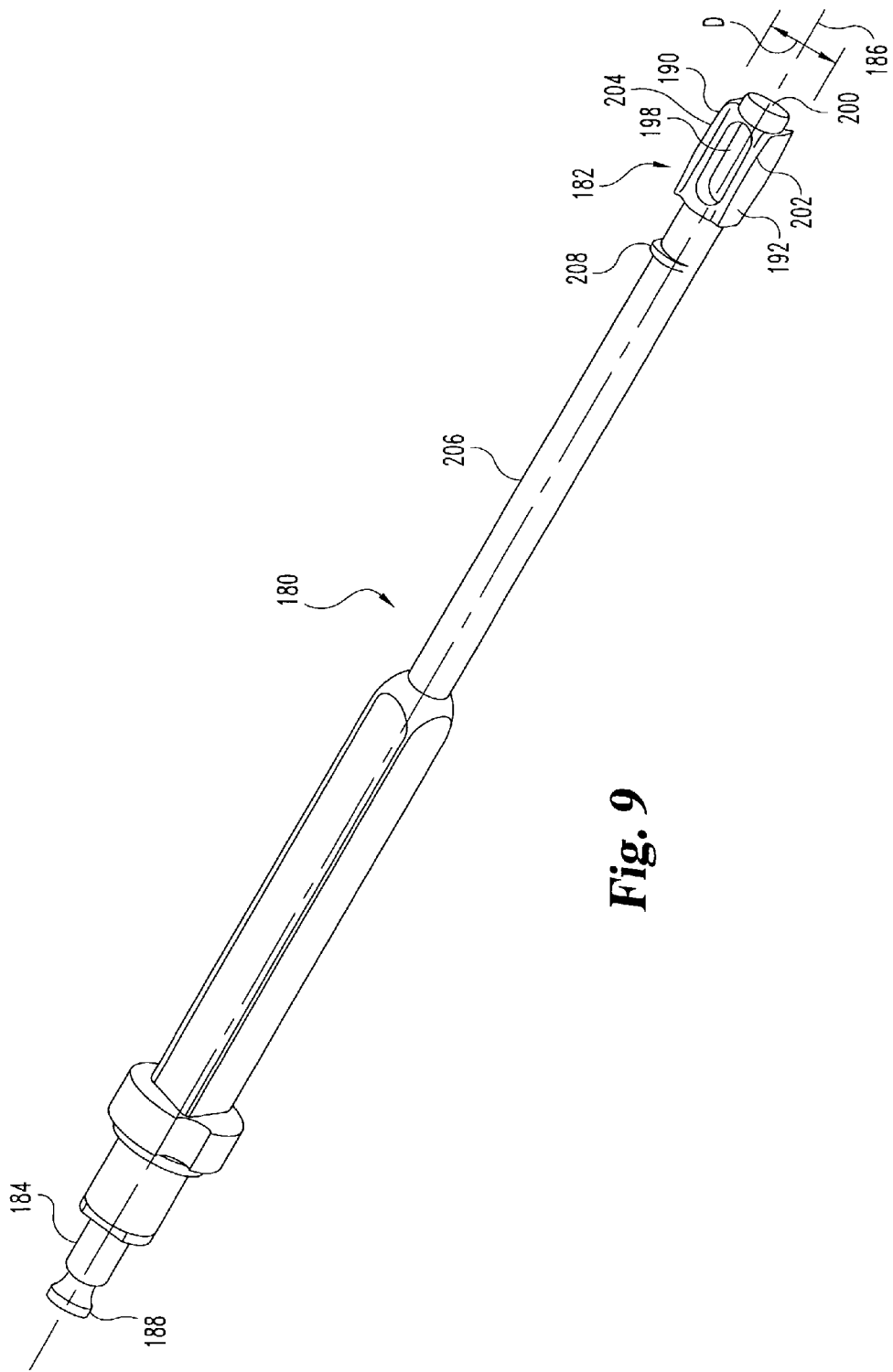
FIG. 9 is a perspective view of one embodiment of a cutting tool according to the present invention.
Figure 10:
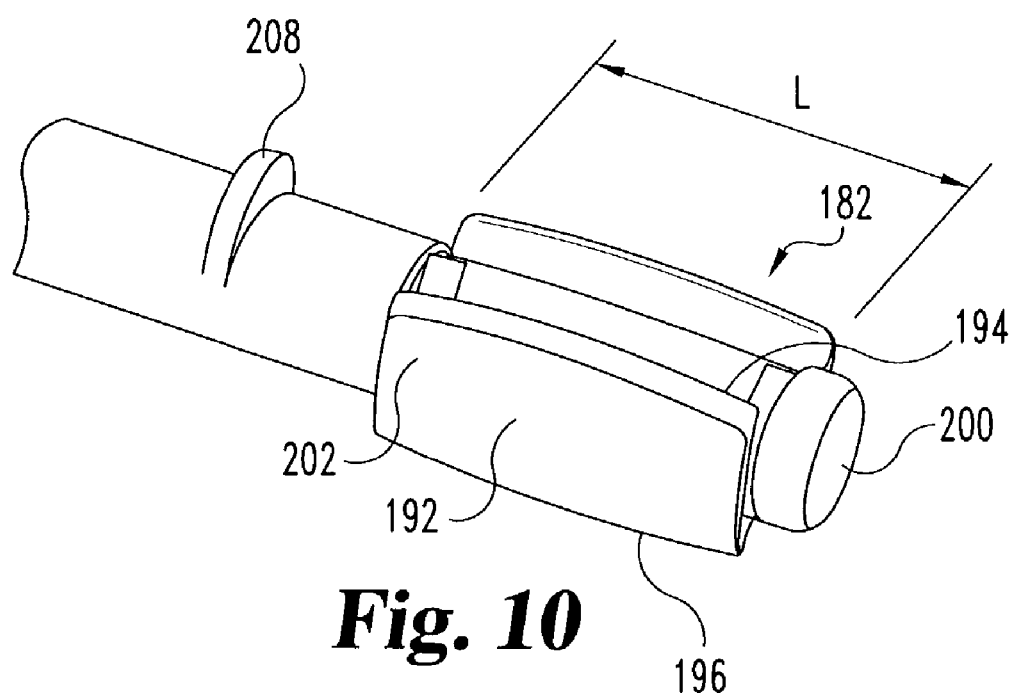
FIG. 10 is a perspective view of the head of the cutting tool illustrated in FIG. 9.

FIG. 8 is a perspective view of one embodiment of an implant holder 150 for use in this invention. Implant holder 150 includes an elongate shaft 152 having a first end 154 adapted to receive a handle and an opposite second end 156 provided with a head 158 for securing a vertebral implant.

Head 158 includes an implant-securing portion 160 to secure an end of an implant (not shown). Securing portion 160 is a generally concave surface or a U-shaped surface. A bottom portion 162 is provided as either a planar surface or slightly convex surface to bear against an endwall of the implant. Projecting longitudinally from bottom portion 162 are a pair of opposing wings 164 and 166, spaced from each other a distance selected to engage opposite longitudinal wall of an included implant such as implant 1 or 80. Bottom portion 162 and wings 164, 166 define a U-shaped cavity 167 adapted to matingly engage a first end and a portion or the lateral sides of an implant. Bottom portion 162 in combination with wings 164 and 166 engage an implant on three sides to cradle the implant in head 158 and control lateral motion of the implant during implantation into the disc space.

A pair of blades 168 and 170 extend inwardly into cavity 167. One blade 168/170 is provided to protrude radially internally from each wing 164, 166. Blades 168 and 170 are provided to engage in grooves 16, 16' of implant 1. It will be understood that blades 168 and 170 can be eliminated from portion 160 to secure alternative embodiments of implants according to the present invention.

Centering pin 172 projects into U-shaped cavity 167 from bottom portion 162. In the illustrated embodiment, centering pin 172 includes a tube 174 having a movable shaft extension 176 received therein. Either or both tube 174 and shaft extension 176 can be provided with external threads. When provided shaft extension 176 is rotatable received within outer shaft 152 toward first end 154 where it connects or engages with a thumb screw or wheel to allow rotation to either withdraw or extend shaft extension 176 through tube 174. In one form, shaft 152 includes am internal thread while shaft extension includes a corresponding external thread to provide longitudinal movement of shaft 152.

Head 158 also includes a depth stop 178 projecting from at least one side in a direction transverse to the longitudinal axis defined by shaft 152. Depth stop 178 is provided to contact the cortical rim of a vertebra adjacent to the disc space and arrest further movement of the attached implant into the disc space.

In use a surgeon can secure implant with implant holder 150, insert or impact it into a disc space, and once inside the space, position the secured implant to a desired location in the disc space—all while the implant remains fixed to the implant holder. After the surgeon has positioned the implant, he or she can readily release the implant from holder 150, leaving the implant at the desired treatment site.

Implants according to this invention may be inserted into an intervertebral space after preparation of the endplates of adjacent vertebrae using cutting tool 180, which will now be described with reference to FIGS. 9–12. Cutting tool 180 includes a cutting head 182, shaft 184 defining a longitudinal axis 186, and handle-engaging portion 188.

Cutting head 182 is attached to the distal end of shaft 184. Cutting head 182 includes a first arm 190 and a second arm 192 extending generally parallel to longitudinal axis 186. Opposing first arm 190 and second arm 192 include two generally smooth, longitudinal faces 202 and 204. Faces 202 and 204 are configured to facilitate insertion of cutting head 182 into the intervertebral space and are generally separated from each other by a distance D. Distance D is selected to be substantially the same as the width of opening 3 in implant 1 or opening 88 in implant 80 measured transverse to the longitudinal axis of the respective implants.

First and second arms 190 and 192 each include first arcuate cutting edge 194 and a second opposite arcuate edge 196. Thus, cutting head 182 includes a total of four cutting edges. First cutting and second cutting edges 194 and 196, respectively, are provided in a configuration to substantially conform to arcuate upper and lower surfaces of implants 1 and 80. Further, first and second arms 190 and 192 and their included first and second cutting edges 194 and 196 are adapted to cut and remove a portion of cortical bone tissue on opposing endplates of adjacent vertebrae V1 and V2, while substantially retaining the natural concave curvature of the endplates. The cutting edges 194 and 196 have a length L selected to avoid cutting cortical rims and preferably the anterior and posterior portions of the endplates proximal to the apophyseal ring. The cavity thus prepared with cutting tool 180 allows intimate contact with a graft material provided either implant 1 or 80 and the spongy bone of the two vertebrae. The bearing surfaces of implant 1 or 80 are disposed adjacent the edges of the openings of the cortical endplates and bear against the remaining portions of the endplates to establish a strong load bearing relationship.

First arm 190 and second arm 192 are generally opposed and define a cavity 198 therebetween for receipt of bony debris generated during the cutting operation. The bony debris collected from the cutting operation can be saved and packed in the opening 3 or 88 of implants 1 and 80, respectively, to promote arthrodesis. Proximal end of first arm 190 and second arm 192 attach to the distal terminus of shaft 184. Opposite ends of first arm 190 and second arm 192 attach to non-cutting portion 200.

Non-cutting portion 200 of cutting head 182 is fixed to the distal end of first arm 190 and second arm 192. Preferably, non-cutting portion 200 has a first dimension transverse to the longitudinal axis substantially the same as distance D to be generally co-extensive with faces 202 and 204 of arms 194 and 196. Non-cutting portion 200 also is adapted to align faces 202 and 204 an equal distance from opposed endplate surfaces of adjacent vertebrae to facilitate removal of equal amounts of cortical bone tissue from adjacent vertebrae. Further, non-cutting portion 200 is adapted to inhibit removal of cortical bone from the anterior cortical bone surfaces of adjacent vertebrae. While the non-cutting portion is depicted as a cylindrical abutment, it is understood that alternative configurations are also included within this invention. Such alternative configurations include spherical, semispherical, frustoconical and the like.

Shaft 184 is rotatably received within sleeve 206. Sleeve 206 includes stop 208 adapted to bear against a vertebral body when the cutting edge is inserted into the intervertebral space. Preferably, stop 208 is adapted to inhibit interference with the inter-spinal processes and associated nerve bodies. In one embodiment, stop 208 is adapted to engage a single vertebral body.

Handle-engaging portion 188 is attached to the proximate end of shaft 184. Handle-engaging portion 188 is adapted to releasably engage a variety of handles known in the art (not shown) to facilitate rotation of shaft 184 and cutting head 182. Alternatively, it is understood that cutting tool 180 can include a handle fixedly attached to the proximal end of shaft 184.

Various non-limiting embodiments of a spinal fixation or fusion procedure of the present invention are next described with reference to FIGS. 11 and 12. One procedure is characterized by: (a) Cutting the vertebrae V1 and V2 with tool 180 to prepare for implantation of implants 1 and/or 80, and (b) Inserting implants 1 and/or 80 between vertebral bodies V1' and V2'. Another more detailed procedure for fusing two vertebrae together is described in terms of the following procedural.

The surgeon exposes the vertebrae in need of fusion using known surgical techniques. The surgeon then exposes the operative level, carefully retracting neural elements. Next the surgeon can perform either a full or partial discectomy to provide sufficient space for the implants in the disc space. If the implants are to be inserted posteriorly, the surgeon inserts, two distractors known in the art between the two vertebral bodies V1, V2 from the rear (posterior). Distractors may be inserted laterally with respect to the cavity provided by the discectomy and then turned 90° so as to spread apart the vertebral bodies and to restore disc height. If a lordotic angle is intended, the distractors may include tapered surfaces intended to establish the desired angulation. Next, one of the distractors is removed.

Figure 11:
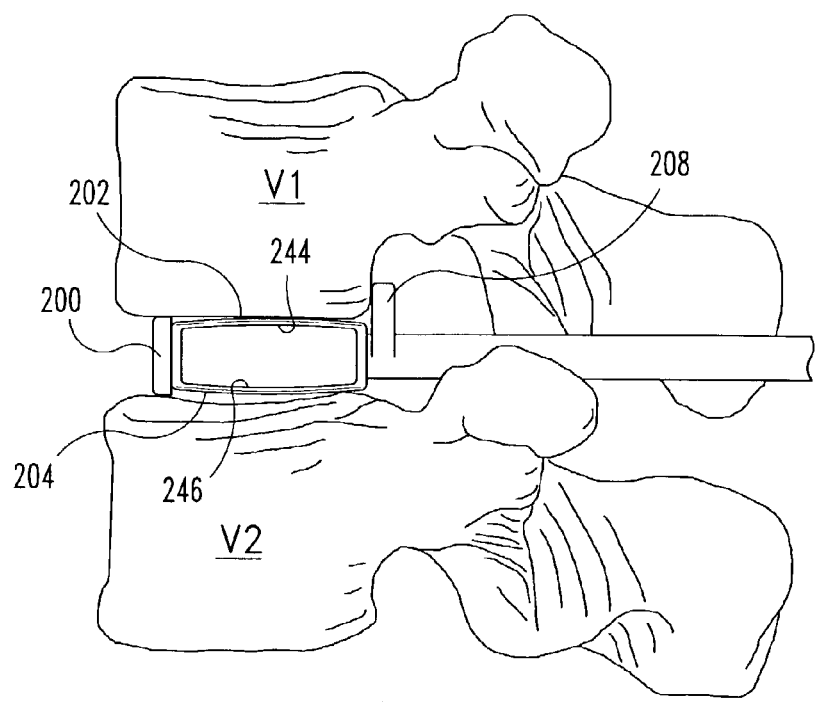
FIG. 11 is an elevated side view in partial section illustrating a portion of the cutter of FIG. 9 received within a disc space.
Figure 12:
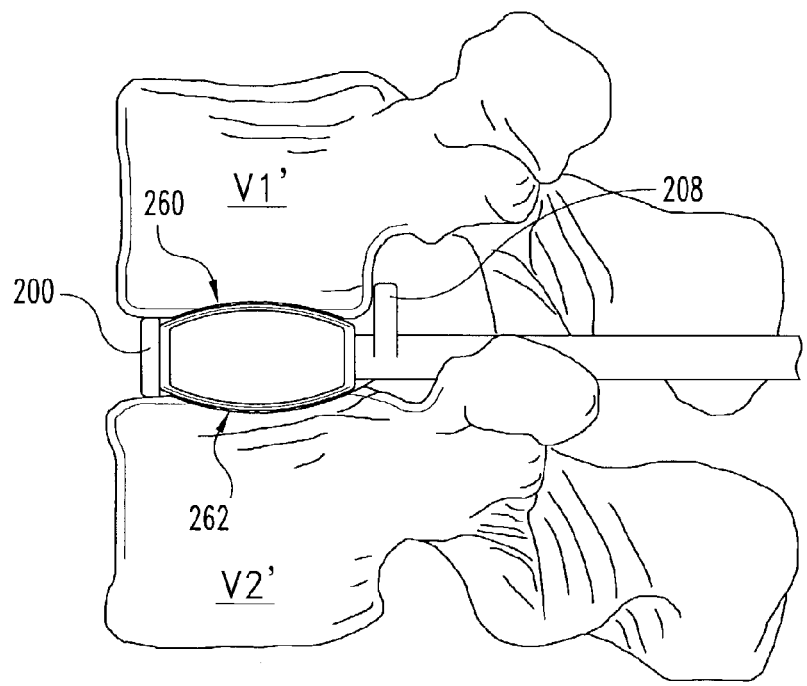
FIG. 12 is an elevated side view in partial section illustrating a portion of the cutter of FIG. 9 rotated 90° within the disc space of FIG. 11.

Referring specifically to FIGS. 11 and 12, the surgeon then inserts cutting tool 180 between vertebral bodies V1 and V2 so that the faces 202 and 204 are in contact with the vertebral endplates as shown in FIG. 11. When the cutting head 182 is correctly positioned in the central region of the cortical endplates, stop 208 abuts the outer surface of V1 or V2, and non-cutting portion 200 is proximal to the interior cortical bone wall of V1 and V2.

Next, the surgeon rotates handle 188, causing cutting head 182 to rotate about longitudinal axis 186. Typically, the surgeon rotates handle 188 through only a partial rotation to engage cutting edges 194 and 196 with the cortical bone of the adjacent endplates and then changes direction to generate an oscillating cutting action. In addition or in the alternative, the surgeon can rotate the cutting edges 194 and 196 to cut the cortical bone. The cutting action continues until the desired or proper amount of vertebral endplate is removed. When non-cutting portion 200 is correctly positioned between interior cortical bone portions of adjacent vertebrae V1 and V2, first cutting edge 194 and second cutting edge 196 cut equally through endplates 244 and 246. This cuts openings 260 and 262 into both vertebral endplates 244 and 246 gouging out a depression that is a concave both in the anterior to posterior direction and in the lateral direction. In preferred embodiments, the maximum lateral dimensions of the opening is selected to be equal to the opening 3 in implant 1 or opening 88 in implant 80. Remaining portions of endplates 244 and 246 bear against non-cutting portion 200 and non-rotating shaft 206. Bony debris generated by the cutting of cortical bone is received in cavity 198 between first arm 190 and second arm 192. Then, the surgeon withdraws cutting tool 180 from the intervertebral space. Bony debris residing in cavity 198 may then be collected and packed inside implant 1 or 80. The surgeon then implants implant 1 (or implant 80), previously filled with either osteogenic material or bony debris, between endplates 244 and 246 from the posterior direction of vertebral bodies V1 and V2. Implant 1 is positioned such that arcuate upper surface 24 and lower surface 26 engage adjacent to cut portions of endplates 244 and 246, while remaining uncut portions adjacent to the cortical rim of endplates 244 and 246 bear against bearing surfaces 8, 8', 9 and 9'. The surgeon then removes the second distractor and repeats the preceding sequences to mount a second implant 1 (or 80) by placing it in position generally parallel to the first implant 1.

Figure 13:
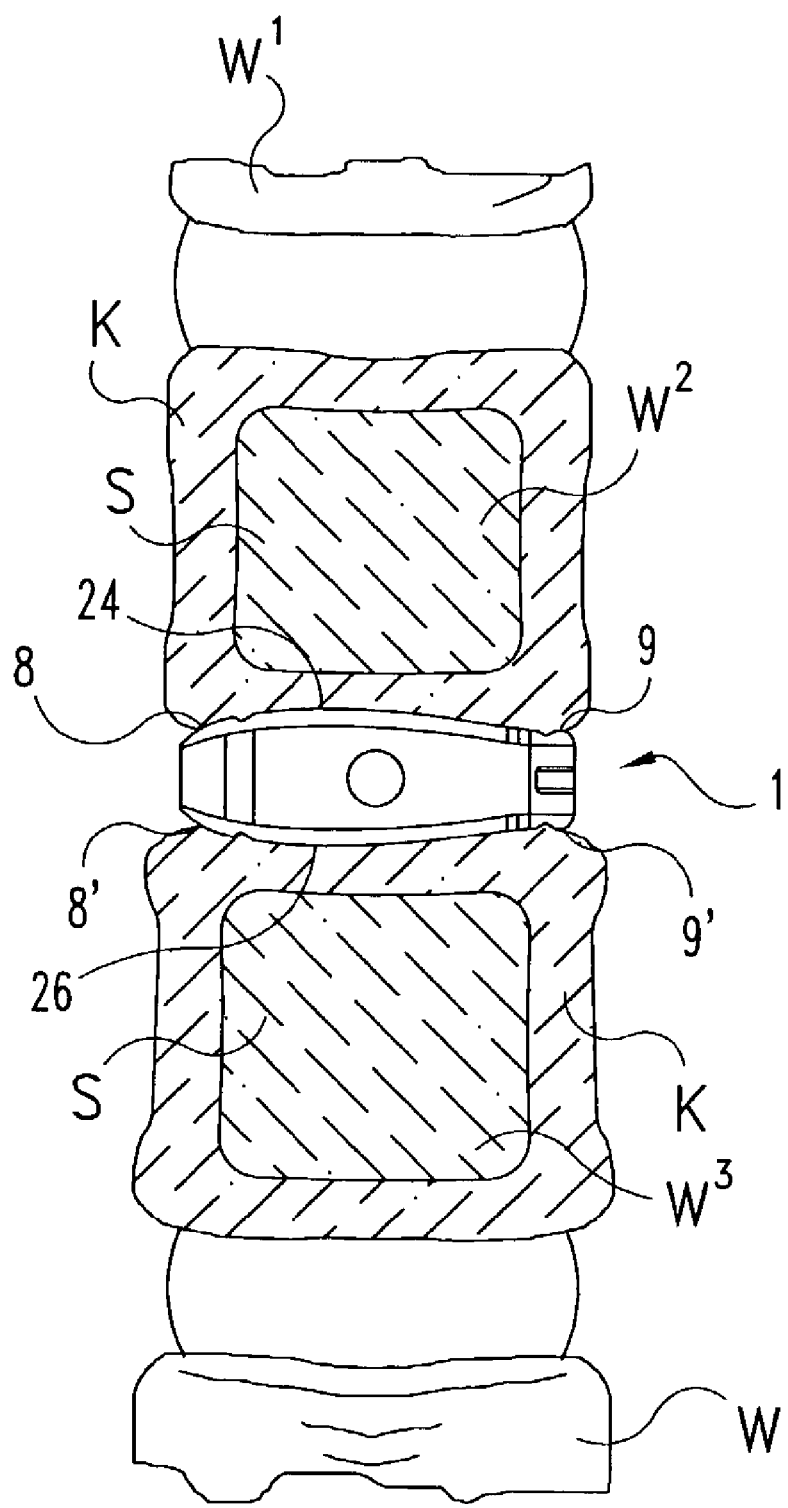
FIG. 13 is a cross-sectional lateral view of a portion of the spinal column with an intervertebral implant positioned between an adjacent pair of vertebrae.

FIG. 13 illustrates a cross-section lateral view of a portion of the spinal column with implant 1 positioned between adjacent vertebrae $W^2$ and $W^3$. It can be observed from the Figure that implant 1 snuggly fits inside the disc space. Upper surface 24 and lower surface 26 contact the opposing endplates substantially along their entire longitudinal length. Bearing surfaces 8, 8', 9 and 9' bear against and support the apophyseal ring structure of the individual vertebrae.

Figure 14:
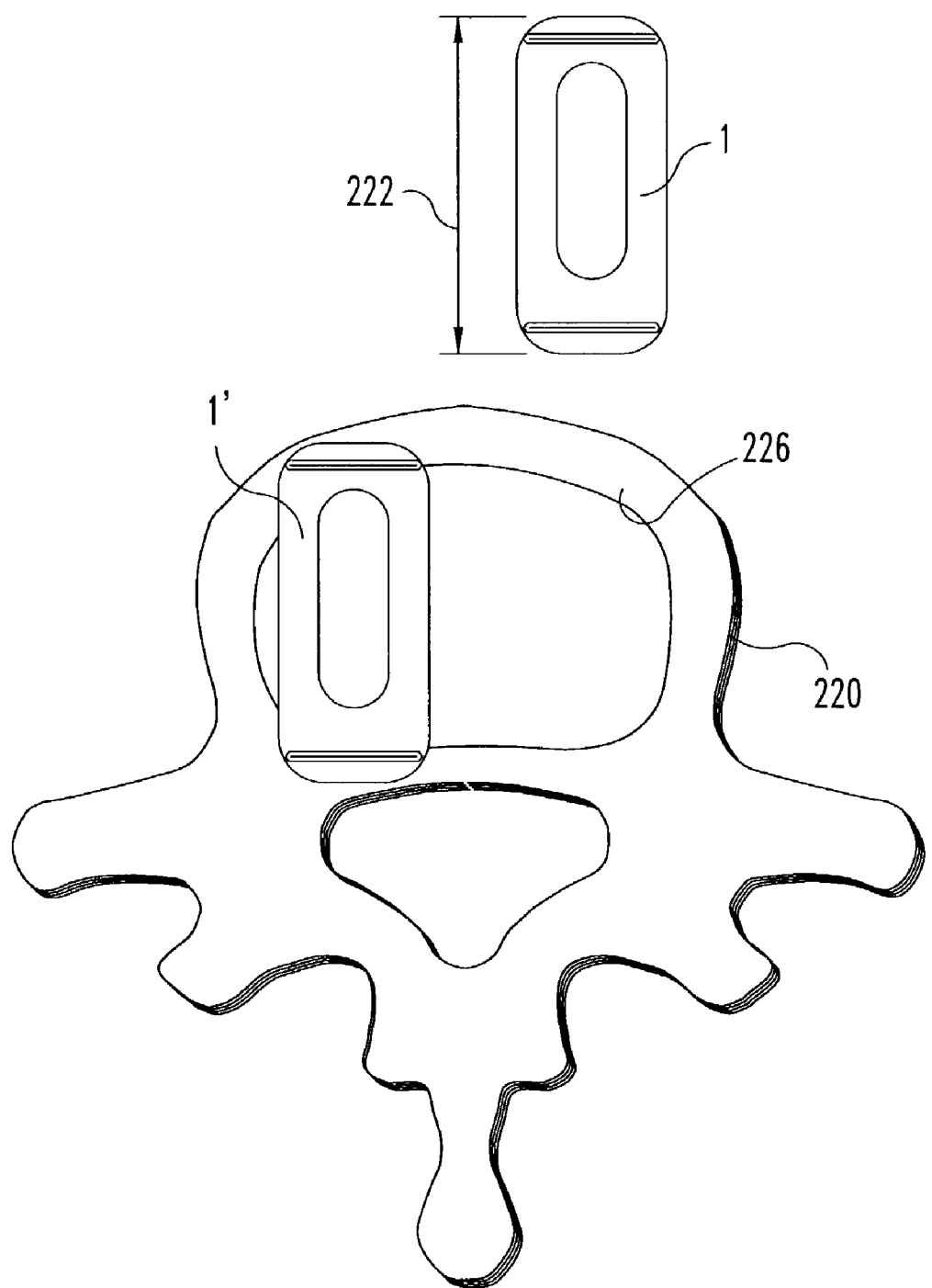
FIG. 14 is a top view of the superior endplate of a lumbar vertebra illustrating the bi-lateral placement of a pair of implants according to the present invention.

FIG. 14 illustrates the bi-lateral placement of a pair of implants 1 and 1' on a profile of a superior endplate of a lumbar vertebra 220. The longitudinal dimension illustrated by reference line 222 of implant 1 is selected to provide a space having a sufficient length to extend across the endplate and position bearing surfaces 8, 8' 9 and 9' opposite the apophyseal ring 226.

In other embodiments, it is envisioned that the described stages may be altered, deleted, combined, repeated, or re-sequenced, as would occur to those skilled in the art. By way of a non-limiting example, the procedure according to the present invention may utilize one or more different tools to prepare the spine for fixation by the implantation of the present invention. In another example, the tools of the present invention may be utilized to prepare a surgical site for an implant.

While this invention has been illustrated and described in detail and drawings and foregoing description, the same is considered to be a list and not restrictive in character, it is understood that only the preferred embodiments have been shown and described and in all changes and modifications that come within the spirit of the invention are desire to be protected.

What is claimed is:

1. A vertebral implant for installation in a disc space comprising a box-shaped, elongated basis body defining a longitudinal axis, which is provided with a cavity extending transverse to the longitudinal axis and through upper and lower bearing surfaces, which cavity is bordered by two planar walls located opposite one another and extending along said longitudinal axis and between said upper and lower bearing surfaces, each of said planar walls having substantially smooth portions extending around said cavity and said planar walls extend between two frontal walls located opposite one another on opposite sides of said cavity, whose crosswise-extending edge surfaces serve as contact surfaces between the vertebrae and the vertebral implant, wherein the two frontal walls of the cavity are formed thicker than both of the longitudinal walls, thereby widening their crosswise-extending edge surfaces, and wherein the implant is made of synthetic material and a groove is formed in each of the crosswise-extending edge surfaces of both of the frontal walls, which groove extends transverse to the longitudinal axis of the basis body, wherein the basis body has receiving means on one frontal end portion for receiving a hand tool such that, with this, a rotational moment about the longitudinal axis of the basis body can be exerted on the basis body and the receiving means has an outwardly open hole formed in the middle of the frontal wall of the basis body and two grooves formed to the side of the hole in the frontal wall of the basis body, which hole is open toward the outside.

2. Vertebral implant of claim 1, wherein the basis body, seen in its widthwise direction, has a respectively longitudinal, externally curved shape.

3. Vertebral implant of claim 1, wherein both of the frontal walls are formed at least two times as thick as the longitudinal walls.

4. Vertebral implant according to claim 1, wherein, in each of the longitudinal walls at least one through hole is formed.

5. Vertebral implant of claim 1, wherein the hole of the receiving means is formed as a threaded hole.

6. Vertebral implant of claim 1, wherein the synthetic material contains elongated carbon fibers.

7. Vertebral implant of claim 1, wherein the synthetic material contains an X-ray contrast agent.

8. An intervertebral implant provided for impaction into a disc space between adjacent vertebrae, said implant defining a longitudinal axis and comprising:
at least one tissue-receiving groove extending transverse to said longitudinal axis;
an elongated cavity bounded by a first endwall at a leading end of the implant and an opposite second endwall at a trailing end of the implant, said first endwall defining a first bearing surface and an opposite second bearing surface and said second endwall defining a third bearing surface and an opposite fourth bearing surface;
an upper surface extending between said first endwall and said second endwall and having an arcuate portion adapted to engage an inferior endplate of a first vertebra;
and an opposite lower surface extending between said first endwall and said second endwall and having an arcuate portion adapted to engage a superior endplate of second vertebrae, wherein said upper and lower surfaces are formed along edges of planar sidewalls on opposite sides of said cavity extending along said longitudinal axis between said first and second endwalls, said sidewalls joining said upper and lower surfaces in a rounded over edge and defining substantially smooth upper and lower surfaces between said cavity and each of said sidewalls, said first endwall further including opposing rounded corners extending from said leading end toward a respective one of said sidewalls, wherein at least one of said first and second end walls include at least one groove extending thereacross in a respective one of said bearing surfaces thereof, wherein said first, second, third and fourth bearing surfaces are each convexly curved along said longitudinal axis and said upper and lower surfaces are substantially smooth and convexly curved between respective ones of said first and third bearing surfaces and said second and fourth bearing surfaces.

9. The implant of claim 8 formed metallic material.

10. The implant of claim 8 formed of a synthetic organic material.

11. The implant of claim 10 wherein the synthetic organic material comprises a biodegradable polymeric material.

12. The implant of claim 10 wherein the synthetic organic material comprises a non-biodegradable polymeric material.

13. The implant of claim 10 wherein the synthetic organic material comprises a reinforcing material selected from the group consisting of: continuous fibers, short fibers, platelets, particles and mixtures thereof.

14. The implant of claim 10 wherein the synthetic organic material comprises a glass fiber, a ceramic fiber or a carbon fiber reinforced polymeric material.

15. The implant of claim 10 wherein the synthetic organic material is selected from the group consisting of: poly(vinyl chloride); poly(methyl (meth)acrylate); polyacrylics; polyamides; polycarbonates; polyesters; polyethylene terephthalate; polysulfones; polyolefins; polyurethanes; polyethers, poly(ether ketones) poly(ether, ether ketones) poly(aryl ether ketones) poly(ether ether ketone ether ketone) and blends and mixtures thereof.

16. The implant of claim 10 wherein the synthetic organic material is selected from the group consisting of: poly (amino acids), polyanhydrides, polycaprolactones, polyorthoesters polylactic acid, poly(lactide-co-glycolide) and blends and mixtures thereof.

17. The implant of claim 8 formed of a ceramic material.

18. The implant of claim 8 wherein said first and second endwall each have a first thickness measured along said longitudinal axis sufficient to maintain a desired disc space height.

19. The implant of claim 8 wherein the first bearing surface, the second bearing surface, the third bearing surface and the fourth bearing surface each include at least one groove extending transverse to the longitudinal axis.

20. The implant of claim 8 wherein said sidewalls are parallel.

21. The implant of claim 8 wherein said first and second bearing surfaces are convexly curved from said cavity to said leading end.

22. An implant for promoting fusion between adjacent vertebrae, said implant comprising:

an elongate body defining a longitudinal axis and having an elongated opening extending therethrough transverse to the longitudinal axis, said body comprising:
a first supporting endwall terminating said body on a first end, said first supporting endwall including convexly curved upper and lower bearing surfaces extending from said opening to rounded over edges at a leading end spaced from said opening along said longitudinal axis;
an opposite second supporting endwall terminating said body on a second end, said first and second supporting endwalls positioned substantially transverse to said longitudinal axis and adapted to bear against cortical bone tissue in opposing endplates of the adjacent vertebrae,
a first planar sidewall and an opposite second planar sidewall extending along said axis on opposite sides of said opening and interconnecting said first supporting endwall and said second supporting endwall, wherein said body includes at least one tissue receiving groove extending from the first sidewall to the second sidewall in at least one of said upper and lower bearing surfaces of said first supporting endwall and rounded corners about said first supporting endwall extending from said leading end toward respective ones of said first and second sidewalls and said sidewalls each include upper and lower surfaces along said opening that are smooth, wherein the first and second sidewalls each terminate in upper arcuate edge and an opposite lower arcuate edge in a direction along said longitudinal axis.

23. The implant of claim 22 wherein the body is formed of a metallic material.

24. The implant of claim 22 formed of synthetic organic material selected from the group consisting of: poly(vinyl chloride); poly((methyl) methacrylate); polyacrylics; polyamides; polycarbonates; polyesters; polyethylene terephthalate; polysulfones; polyolefins; polyurethanes; polyethers, poly(ether ketones) poly(ether, ether ketones) poly(aryl ether ketones) poly(ether ether ketone ether ketone) and blends and mixtures thereof.

25. The implant of claim 22 formed of synthetic organic material selected from the group consisting of: a poly(amino acid), a polyanhydride, a polycaprolactone, a polyorthoester, a polylactic acid, a poly(lactide-co-glycolide) and blends and mixtures thereof.

26. The implant of claim 22, wherein the body is formed of a biodegradable polymeric material.

27. The implant of claim 22, wherein the body is formed of a non-biodegradable polymeric material.

28. The implant of claim 22, wherein the body is formed of a reinforced composite.

29. The implant of claim 28 wherein the reinforced composite comprises a glass fiber, a ceramic fiber or a carbon fiber reinforced polymeric material.

30. The implant of claim 22 wherein the body is formed of a ceramic material.

31. The implant of claim 22, wherein said first and second supporting endwalls each has a thickness, measured along said longitudinal axis, sufficient to maintain a desired disc space height.

32. The implant of claim 22 wherein said first sidewall and said second sidewall each include an aperture into said opening.

33. The implant of claim 22 wherein said first and second bearing surfaces each comprising tissue receiving groove.

34. The implant of claim 22 wherein said sidewalls are parallel.

35. The implant of claim 33 wherein said bearing surfaces are adapted to matingly engage in opposing apophyseal rings portions of the adjacent vertebrae.

36. The implant of claim 22 wherein the first and second sidewalls define a lordotic profile.

37. The implant of claim 22 wherein said upper surface and said lower surface extend between said first and second supporting endwalls.

38. A vertebral implant for installation in a disc space comprising a box-shaped, elongated basis body defining a longitudinal axis, which is provided with a cavity elongated along said longitudinal axis, said cavity extending transverse to the longitudinal axis and through opposite upper and lower bearing surfaces, which cavity is bordered by two planar sidewalls located opposite one another and extending parallel to one another along said longitudinal axis and between said upper and lower bearing surfaces, said cavity further bordered by a first endwall and a second endwall located opposite one another and extending transversely to said longitudinal axis between said sidewalls, said first endwall including rounded corners extending from a leading end toward respective ones of said sidewalls and from said leading end to said upper and lower bearing surfaces, wherein at least one of said upper bearing surface and said lower bearing surface includes at least one groove extending transverse to the longitudinal axis across at least one of said first and second endwalls and said upper and lower bearing surfaces are smooth along said sidewalls, wherein said upper bearing surface and said lower bearing surface are each convexly curved along said longitudinal axis.

39. The implant of claim 38, wherein said first and second endwalls are formed thicker than both of the sidewalls.

40. The implant of claim 38, wherein said upper and lower bearing surfaces are convexly curved from said cavity to said first endwall.

41. The implant of claim 38, wherein said sidewalls join said upper and lower surfaces in a rounded over edge.

42. The implant of claim 41, wherein said cavity includes a shape in plan view in the form of an elongated rectangle with a semi-circular end adjacent each of said endwalls.

* * * * *